(12) United States Patent
Soukup

(10) Patent No.: US 8,524,936 B2
(45) Date of Patent: Sep. 3, 2013

(54) MANUFACTURING PROCESS FOR SITAGLIPTIN FROM L-ASPARTIC ACID

(76) Inventor: Milan Soukup, Sarasota, FL (US)

( * ) Notice: Subject to any disclaimer, the term of this patent is extended or adjusted under 35 U.S.C. 154(b) by 264 days.

(21) Appl. No.: 13/068,713

(22) Filed: May 18, 2011

(65) Prior Publication Data

US 2012/0123144 A1    May 17, 2012

(51) Int. Cl.
*C07C 269/00* (2006.01)
*C07C 227/10* (2006.01)

(52) U.S. Cl.
USPC ............. 560/30; 544/1; 544/224; 544/336; 548/100; 562/449

(58) Field of Classification Search
USPC ............. 544/1, 224, 336, 349; 548/100; 560/30, 38; 562/449
See application file for complete search history.

(56) References Cited

U.S. PATENT DOCUMENTS

| | | |
|---|---|---|
| 6,699,871 B2 | 3/2004 | Edmondson et al. |
| 7,125,873 B2 | 10/2006 | Edmondson et al. |
| 7,307,164 B2 | 12/2007 | Brockunier et al. |
| 7,326,708 B2 | 2/2008 | Zypes et al. |
| 7,468,459 B2 | 12/2008 | Xiao et al. |

OTHER PUBLICATIONS

L.A.Sorbera et al. Druf of the Future 2005, 30, 337.
G. Sun et al. Chinese J. Pharm. 2008, 39, 383.
K.Dooseop et al. J. Med. Chem. 2005, 48, 141.
L.L.Zeng et al. Chinese Chem. Lett. 2009, 20, 1397.
Y.E.Fei et al. Chinese J. Syn. Chem. 2010, 6, 767.
K.B.Hansen et al. JACS 2009, 131, 8798.
D. Steinhuebel et al. JACS 2009, 131, 11316.
A.M. Clausen et al. Org. Proc Res. Dev. 2006, 10, 723.
K.B.Hansen et al. ibid. 2005, 9, 634.
F.Xu Proc. Chem. Pharm. Ind. 2008, 333.
D.Kim et al. Bioorg. Med. Chem. Lett. 2007,17,3373.
J.A.Hatnean et al. Organometallics 2010, 29, 6077.
Feng Liu et al. J. Chem. Res. 2010, 230.
Feng, Liu et al. J. Chem. Res. 2010, 517.
A.B.Hughes et al. Helv. Chim. Acta 2006, 89, 2611.
J.E.Baldwin et al. Tetrahedron 1986,42,6551.
M. Seiki et al. Chem. Pharm. Bull. 1986, 34, 4516.
O. Itoh et al. Synthesis 1999,3,423.
M. Abarbri et al. Tetrahedron Lett. 1999, 40, 7449.
J.Liu et al. ibid. 2002, 43, 8223 ibid. 2002, 43, 8223.
C.K. Savile et al. Science 2010, 329, 305.
Y.Zhu et al. Europ. J. Med. Chem. 2010, 45, 4953.
R. Angelaud et al. J. Org. Chem. 2005, 70, 1949.
G. Tasnadi et al. Org. Biomol. Chem. 2010, 8, 793.
M.Kubryk et al. Tetrahedron Asymmetry 2006, 17, 205.

*Primary Examiner* — Johann R Richter
*Assistant Examiner* — Blaine G Doletski

(57) ABSTRACT

The present invention relates to a novel manufacturing process of pharmaceutically active compound of formula I used as oral anti-diabetic drug. Starting from L-aspartic acid derivate of formula IV the invention describes preparation of the chiral (R)-β-amino acid of formula II known as a precursor in the synthesis of Sitagliptin (formula I).

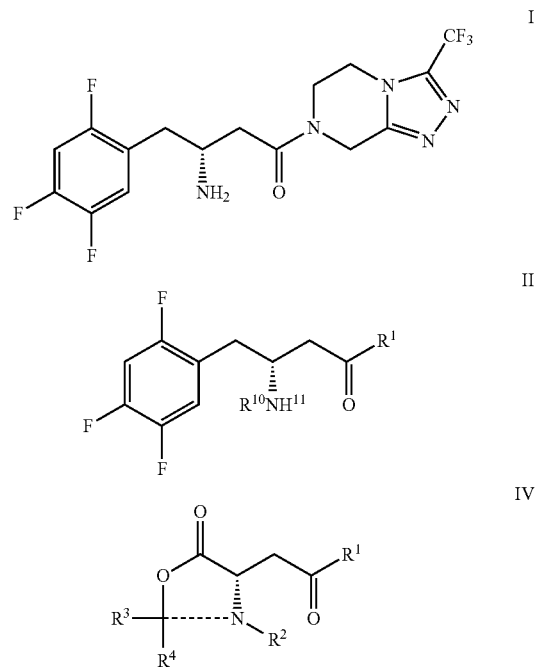

6 Claims, No Drawings

MANUFACTURING PROCESS FOR SITAGLIPTIN FROM L-ASPARTIC ACID

BACKGROUND OF THE INVENTION

Sitagliptin (compound of formula I) is an oral antihyperglycemic drug used for treatment of diabetes.

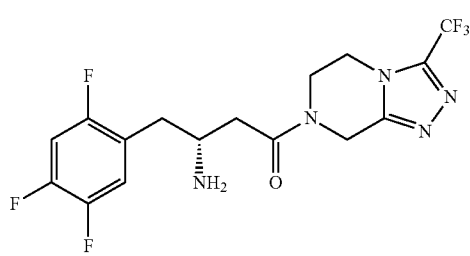

The pharmacological activity of Sitagliptin is attributable to (R)-enantiomer and many syntheses have been recently developed to prepare the enantiomerically pure compound (U.S. Pat. No. 6,699,871, U.S. Pat. No. 7,307,164, US20060052382, U.S. Pat. No. 7,468,459, U.S. Pat. No. 7,326,708, U.S. Pat. No. 7,125,873, Drug of the future 2005, 30, 337, Chinese J. Pharm. 2008, 39, 383). Although the synthesis of the heterocyclic fragment containing four nitrogen atoms in 5-/6-membered ring system has been already sufficiently resolved (e.g. J. Med. Chem. 2005, 48, 141 or Drug of the future 2005, 30, 337), there is still a need for a better and more cost efficient synthesis of the second building block, the (R)-β-amino acid of formula IIa.

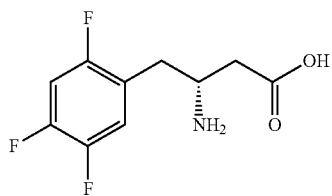

For the preparation of this (R)-β-amino acid and derivates thereof many different approaches have been published but in all the chiral center has been specifically formed during the synthesis. Originally (R)-enantiomer has been prepared via resolution of a racemate (Chinese Chem. Lett. 2009, 20, 1397, Chinese J. Synth. Chem. 2010, 6, 767 and Org. Biomol. Chem. 2010, 8, 793, WO2010/131025 and WO2010/122578). Later on (R)-enantiomer has been obtained stereo specifically via asymmetric homogeneous hydrogenation of an enamine precursor using various chiral Rh-catalysts (J. Am. Chem. Soc. 2009, 131, 8796, ibid. 2009, 131, 11316, Org. Proc. Res. Dev. 2006, 10, 723, ibid. 2005, 9, 634, Proc. Chem. Pharm. Ind. 2008, 333 and Tetrahedron Asymmetry 2006, 17, 205 and WO2010/078440). In another approach an enamine precursor containing on nitrogen alkyl substituent as a chiral auxiliary e.g. phenethylamine has been diastereo selectively hydrogenated (Bioorg. Med. Chem. Lett. 2007, 17, 3373, J. Am. Chem. Soc. 2004, 126, 3048 and J. Chem. Res. 2010, 230). Also biocatalytic asymmetric synthesis using transaminase and β-keto acid as the starting material has been published (Science 2010, 329, 305). Further approach via β-hydroxy acid and β-lactam has been reported in J. Org. Chem. 2005, 70, 1949.

No synthesis of Sitagliptin has ever been reported using a chiral starting material from a chiral pool: Recently X. Pan et al. (J. Chem. Res. 2010, 517) realized that configuration of (R)-β-amino acid of formula IIa corresponds the configuration of inexpensive natural L-aspartic acid which could be used as a starting material. Thus, instead of forming the chiral center by expensive stereoselective method, the chiral center of L-aspartic acid has been successfully used first time to generate the chiral center in the (R)-β-amino acid of formula IIa. Nevertheless, the disclosed process as reported by Pan suffers with many drawbacks. Too many steps are necessary just to form an appropriate intermediate of L-aspartic acid which has been then successfully reacted with aromatic Grignard reagent derived from 1,2,4-trifluorobenzene. Although in this concept inexpensive starting material, L-aspartic acid is used, still too many steps are involved and consequently further improvements are required. For a cost efficient manufacture of Sitagliptin there is a clear need for a new process in which either inexpensive L- or racemic aspartic acid would be used as a starting material.

SUMMARY OF THE INVENTION

The present invention discloses a novel technical process for the manufacture of enantiomerically pure (R)-β-amino acid of formula II from inexpensive, readily available L-aspartic acid as shown in Scheme 1:

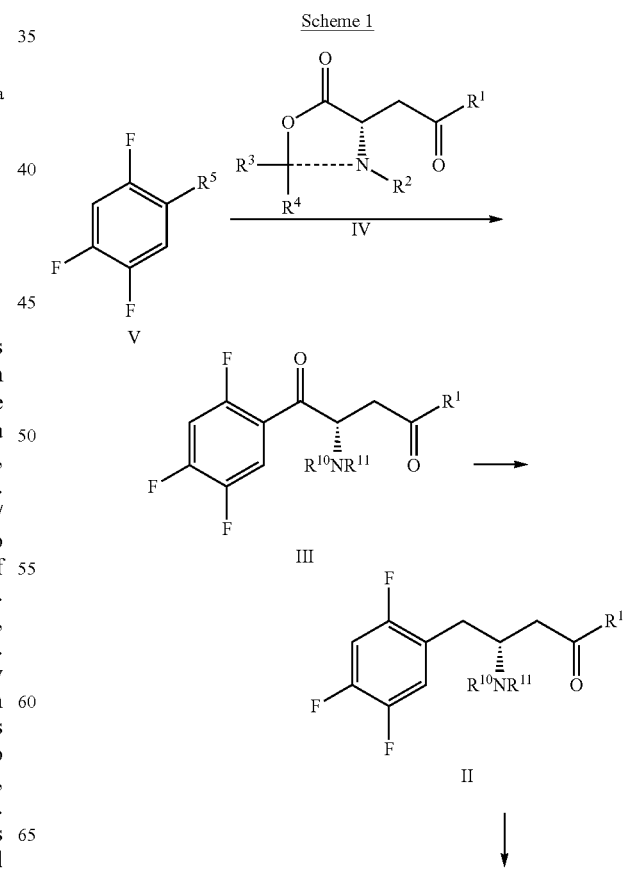

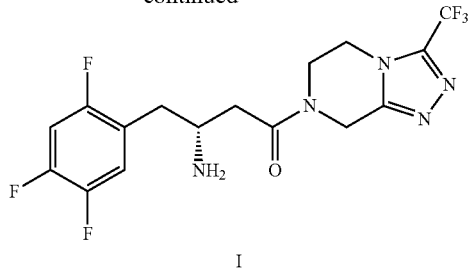

I

Treatment of N-protected L-aspartic acid with a carbonyl containing compound provides cyclic compound of formula IV which undergoes readily either Lewis acid catalyzed Friedel-Crafts type arylation with a compound of formula V, wherein $R^5$ is hydrogen, or it reacts smoothly with aryl organometallic compound of formula V, wherein $R^5$ is a metal containing group as e.g. Grignard reagent, providing ketone intermediate of formula III which can be easily reduced forming the enantiomerically pure (R)-β-amino acid of formula II. Optionally, if an appropriate solvent is used, in which a salt of S-configured compound of formula III is only limited soluble, then in the presence of a stoichiometric amount of a chiral acid and catalytic amount of an aldehyde, a process called crystallization induced asymmetric transformation can be carried out which converts not sufficiently enantiomerically pure or even racemic compound of formula III completely into the (S)-configured compound of formula III with high optical purity (>99% ee).

DETAILED DESCRIPTION OF THE INVENTION

The present invention claims a process (Scheme 1) for preparation of a compound of formula II, having the configuration as given in the formula,

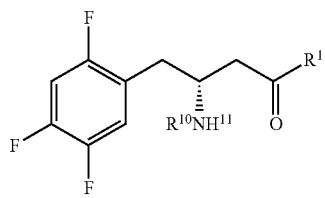

II wherein $R^1$ represents hydroxy, alkoxy, aryloxy, alkylaryloxy, arylakyloxy, preferably methoxy, ethoxy, benzyloxy, or
—$NR^6R^7$, wherein $R^6$ and $R^7$ are independently from each other hydrogen, lower alkyl, alkylaryl, arylalkyl, preferably —$NH_2$, —$NMe_2$, —Ndibenzyl, or in particular $R^6$ and $R^7$ can form together with N a 5- or 6-membered heterocyclic ring which may contain one or more heteroatoms selected from N or O and, which can be unsubstituted or substituted, preferably 4-alkyl-oxazolidin-2-one-3-yl, containing also a chiral center as 4(R)- or 4(S)-benzyl-oxazolidin-2-one-3-yl, or
—$NR^8OR^9$, wherein $R^8$ and $R^9$ are independently from each other hydrogen, lower alkyl, alkylaryl, arylalkyl, preferably —NMeOMe, or in particular $R^8$ and $R^9$ can form together with N and O a 5- or 6-membered heterocyclic ring which may contain one or more heteroatoms selected from N or O and, which can be unsubstituted or substituted, containing also a chiral center, and $R^{10}$ and $R^{11}$ are independently from each other hydrogen, alkyl, aryl, alkylaryl, arylalkyl, preferably benzyl, mono-, di- or tri-methoxybenzyl, or other N-protective group, in particular one which together with N forms an amide or carbamate as —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl C(O)CMe$_3$, C(O)OEt and C(O)OiPr, —C(O)Obenzyl (Cbz) or —C(O)Otert.-butyl (BOC), comprising following steps:
a) reaction of the compound of formula IV, having the configuration as given in the formula,

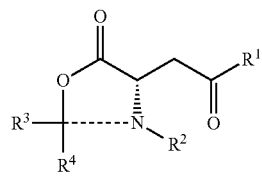

IV wherein $R^1$ is the same as defined for compound of formula II, and
i) when the dotted CN bond is a double bond, then
$R^2$ and $R^3$ are void, and
$R^4$ is hydrogen, alkyl, aryl, alkylaryl, arylalkyl, preferably hydrogen, phenyl, benzyl, methyl, trifluoromethyl,
or
ii) when the dotted CN bond is a single bond, then
$R^2$ is hydrogen, alkyl, aryl, alkylaryl, arylalkyl, preferably benzyl, mono-, di- or tri-methoxybenzyl, or other N-protective group, in particular one which together with N forms an amide or carbamate as —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl C(O)CMe$_3$, C(O)OEt and C(O)OiPr, —C(O)Obenzyl (Cbz) or —C(O)Otert.-butyl (BOC, and
$R^3$ and $R^4$ are either independently from each other hydrogen, lower alkyl, aryl, alkylaryl, arylalkyl, preferably hydrogen, phenyl, trifluoromethyl, or
$R^3$ and $R^4$ are one oxygen atom forming together carbonyl function C=O,
with a compound of formula V,

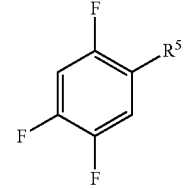

V wherein $R^5$ is
i) either hydrogen, in aprotic organic solvent, preferably chlorinated hydrocarbons as methylenechloride or aliphatic hydrocarbons as hexane or heptane, in the presence of a catalyst used for Friedel- Crafts reaction, preferably bortrifluoro etherate, metal halide as Al-, Zn-, lanthanide- and Bi-halides, ii) or a metal containing group such as —Li, —Na, —Mghalide (Grignard reagent), Znhalide, Mnhalide, cuprate, —Cuhalide, —Cehalide, boronic acid as —B(OH)$_2$, preferably —Li or —MgBr, in inert organic solvent, preferably THF, providing a compound of formula III,

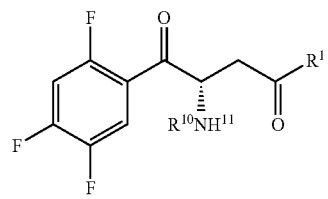

III wherein $R^1$, $R^{10}$ and $R^{11}$ are the same as defined for compound of formula II;

b) reduction of the carbonyl function in the benzyl position in the compound of formula III, simultaneously or in separate steps, providing compound of formula II;

c) protection or removal of N-protective group(s) as they are defined for $R^{10}$ and $R^{11}$ in the compound of formula II.

The starting compound of formula IV can be prepared in many different ways as thoroughly reported in literature:

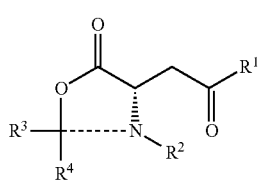

IV 1,3-oxazolidinon-5-ones derived from L-aspartic acid can be prepared in 2 steps from L-aspartic acid as reported in e.g. Helv. Chim. Acta 2006, 89, 2611 or Tetrahedron 1986, 42, 6551. After N-protection of L-aspartic acid with e.g. Cbz-group, treatment of N-protected L-aspartic acid with an aldehyde or ketone, preferably with formaldehyde, in the presence of a catalytic amount of an acid provides corresponding 1,3-oxazolidinones in very high yield.

Azlactones derived from L-aspartic acid can be prepared from L-aspartic acid by reaction with an acyl chloride followed by subsequent cyclization using a suitable dehydration agent (Chem. Pham. Bull. 1986, 34, 4516).

N-Carboxy anhydrides of L-aspartic acid can be readily obtained from a half ester of L-aspartic acid by treatment with phosgene (Synthesis 1999, 3, 423).

In the preferred embodiment of the invention the compound of formula V, wherein $R^5$ is a metal containing group, especially an alkali or earth alkali metallic radical, as e.g. lithium, sodium, potassium or a group of formula Mg-halogen, —Znhalogen, -Cer(halogen)$_2$ or boronic acid as —B(OH)$_2$, preferably —Li or —MgBr or —Mg ate complex, is prepared from corresponding aromatic halide (a compound of formula V, wherein $R^5$ is a halide, preferably bromide) and it is used in situ in an inert solvent, such as THF etc., at a temperature range of −78° C. to 30° C. similar as reported in J. Chem. Res. 2010, 517 or Tetrahedron Lett. 1999, 40, 7449 or ibid. 2002, 43, 8223 or J. Org. Chem. 2001, 66, 4333.

If the compound of formula IV should contain an acidic hydrogen, the organometallic reagent of formula V has to be used in excess or prior addition of the reagent a selective deprotonation with another inorganic or organic base, preferably metal hydride or lithium amide or alkyl magnesium halide as i-PrMgCl, has to be done to avoid an excess of the expensive reagent of formula V.

In the further embodiment of this invention, instead of addition reaction of the organometallic compound of formula V, wherein $R^5$ is metal containing group to compound of formula IV, the "polarity of the reaction" can also be reversed: In such a case the compound of formula V, wherein $R^5$ is hydrogen, can be reacted with compound of formula IV in an inert aprotic organic solvent, preferably chlorinated hydrocarbons as methylenechloride or dichloroethane or aliphatic hydrocarbons as hexane or heptane, in the presence of a catalyst as commonly used for Friedel-Crafts reaction as e.g. bortrifluoro etherate, metal halide(s), preferably aluminium chloride, Zn-, lanthanide- and Bi-halides (s. example in Tetrahedron Letters 2003, 44, 2937, ibid. 2003, 44, 5343, Tetrahedron 2004, 60, 10843), under standard Friedel-Crafts conditions. As solvent aprotic organic solvent, preferably chlorinated hydrocarbons, preferably methylenechloride or dichloroethane, or aliphatic hydrocarbons, preferably hexane or heptane, can be used. Reaction temperature in a range of −78° C. to 90° C., preferably −10° C. to 35° C., is dependent on specific substitution pattern of the compound of formula IV and the solvent.

The reduction or hydrogenation of 4-oxo group in compound of formula III, can be achieved either simultaneously or in separate steps. The preferred reduction method is definitely hydrogenation in the presence of homogeneous or heterogeneous hydrogenation catalysts, preferably Pt or Pd on charcoal or Ra—Ni or various Rh-catalysts. Alternatively reduction with metal hydrides, preferably sodium or lithium borohydride or trialkylsilanes in the presence of acid, preferably triethylsilane in the presence of triflic or trifluoroacetic acid or Lewis acid as bortrifluoro etherate, ZnCl$_2$, AlCl$_3$ or TiCl$_4$ at reaction temperature between −78 C until reflux can also be carried out.

By the organometallic addition of the compound of formula V to a compound of formula IV or in Friedel-Crafts reaction no major racemization has been observed. Nevertheless, additional recrystallization of the compound of formulas III or IV from an appropriate solvent may further be useful to increase the enantiomeric excess (% ee).

In the further embodiment of the invention, if the enantiomerically purity of the compound of formula III might not be sufficient high (ee <95%), a process known as crystallization induced asymmetric transformation can be applied to increase the enantiomeric excess (% ee). According to this process not only enantiomerically enriched but even racemic compound of formula III can be fully converted into enantiomerically pure (S)-compound of formula III. This process is possible because the carbonyl function at C(4)-atom facilitates racemization at the neighboring chiral center bearing amino function. Adding a suitable chiral acid HX, preferably in stoichiometric amount, in the presence of catalytic amount of a suitable aldehyde to a compound of formula III in a suitable solvent, in which the (S)-configurated compound has only a limited solubility, a process known as crystallization induced asymmetric transformation allows that from the precipitate only enantiomerically pure HX salt of the (S)-compound of formula III can be isolated.

As a chiral acid H—X preferably (1R or 1S)-10-camphorsulfonic acid or (1R or 1S)-3-bromocamphor-8-sulfonic acid in stoichiometric amount can be used. The reaction can be carried out at any temperature, but preferably in boiling solvents, in alcohol, dialkylether, aromatic hydrocarbon, acetone, acetic acid, acetonitrile or nitromethane, where the HX salt of the (S)-compound of formula III has only limited solubility. Under these conditions all starting material containing compound of formula III, initially in the form as enantiomerically enriched or as racemate, undergoes crystallization induced asymmetric transformation providing in the precipitate pure HX salt of the compound of formula III, having specifically only the (S)-configuration Collecting the enantiomerically pure HX-salt of (S)-configurated compound of formula III from the precipitate, converting this salt into (S)-compound of formula III by treatment with suitable organic or inorganic base. If an appropriate solvent is used, this process converts finally all material into enantiomerically pure (S)-compound of formula III.

The reaction temperature for crystallization induced asymmetric transformation can be in the range of −10° C. until boiling temperature of the used solvent. Preferably reflux temperature has been used. Dependent on a solvent catalytic amount, preferably 5-10 mol.-%, of an aldehyde or ketone, preferably aromatic aldehyde as benzaldehyde or derivative thereof, can be used.

When referring to compounds described in the present invention, it is understood that references are also being made to salts thereof, preferably to H—X salts, wherein H—X is a suitable chiral acid.

In this invention a characteristic of protective groups are that they can be removed readily (without the occurrence of undesired secondary reactions) for example by solvolysis, reduction, or alternatively under physiological conditions (as e.g. enzymatic cleavage or formation). Different protective groups can be selected so that they can be removed selectively at different stages of the synthesis while other protective groups remain intact. The corresponding alternatives can be selected readily by a person skilled in the art from those given in the standard reference works mentioned in literature (as e.g. Mc Omie "Protective Groups in Organic Chemistry" or Green et al. "Protective Groups in Organic Synthesis") or in the description or in the claims or the Examples.

For the purpose of this disclosure, a compound is considered to be "enantiomerically pure" if the content of one isomer is higher than 95%, preferably 99%.

The example are provided to illustrate particular aspects of the disclosure and do not limit the scope of the present invention as defined by the claims.

EXAMPLES

Determination of optical purity was carried out with HPLC using chiral columns as Chiralcel OJ-H, Chiralpak AS-H or Chiralpak AD-H from Daicel Chem. Ind. In some cases the optical purity was also determined with NMR-Spectroscopy using chiral Eu-shift reagent. If not mentioned otherwise, all evaporations are performed under reduced pressure, preferably between 5-50 Torr, in some case even under high vacuum. The structure of final products, intermediates and starting materials is confirmed by standard analytical methods, e.g. spectroscopic characteristics as MS or NMR or IR. Abbreviations used are those conventional in the art.

Example 1

(3R)-3-amino-4-(2,4,5-trifluorophenyl)-butyric acid hydrochloride (IIa)

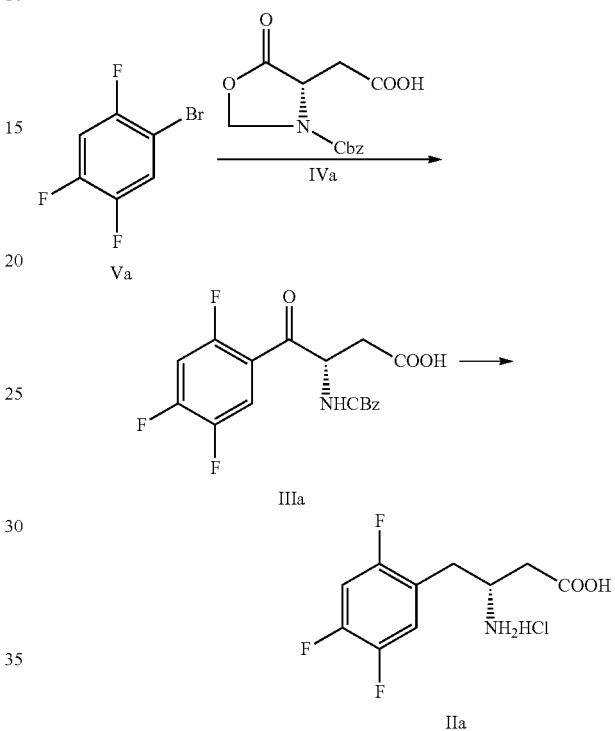

In inert atmosphere to a solution of 1-bromo-2,4,5-trifluorobenzene (Va, 21 g) in THF (75 ml) cooled to −20° C. under good stirring i-PrMgBr solution (110 ml, 1M in THF) was slowly added that the reaction temperature remained at −20° C. and the solution then stirred at the same temperature for ca. 1 hr.

In another flask in inert atmosphere under stirring compound IVa (28 g, prepared according to Helv. Chim. Acta 2006, 89, 2611) was dissolved in THF (75 ml), the solution cooled to −20° C., the slurry then treated with i-PrMgBr solution (110 ml, 1M in THF) at −20° C. and afterwards stirred for 20 min. To this solution within ca. 0.5 hr Grignard solution prepared above from the compound Va was slowly added at −20° C., the cooling then removed, the reaction warmed up to it and stirred for 4 hrs. After the reaction was completed (TLC) the reaction mixture was poured on a mixture of ice and 1N—HCl (ca. 100 ml), the aqueous phase extracted 3 times with ethylacetate (3×200 ml), the combined organic phases dried over MgSO$_4$, filtered and evaporated under reduced pressure to afford a pale yellow semicrystalline material IIIa (31 g, 84% yield) which was used directly for the reduction step.

To a solution of crude compound IIIa (31 g) in methanol (200 ml), after addition of conc.—HCl (2 ml) and 10% Pd—C (500 mg), the reaction slurry was hydrogenated at rt under vigorous stirring and slightly elevated hydrogen-pressure (4 bar) until the starting compound IIIa completely disappeared (3 hrs). After filtration of the catalyst, the filtrate was concentrated under reduced to provide the title compound IIa as a yellow solid: 19.9 g (70% yield calc. from IVa) which was then recrystallized from hot TBME/ethanol mixture providing the title compound IIa with 99.1% ee. Anal. calculated for $C_{10}H_{11}ClF_3NO_2$: C, 44.54; H, 4.11; Cl, 13.15; F, 21.14; N, 5.19; O, 11.87. Found: C, 44.52; H, 4.21; Cl, 13.08; F, 21.09; N, 5.11; O, 12.0. The analytical data of II a have been identical with published (Europ. J. Med. Chem. 2010, 45, 4953 and Org. Biomol. Chem. 2010, 8, 793).

Example 2

(3R)-3-methoxycarbonylamino-4-(2,4,5-trifluorophenyl)-butyric acid (IIb)

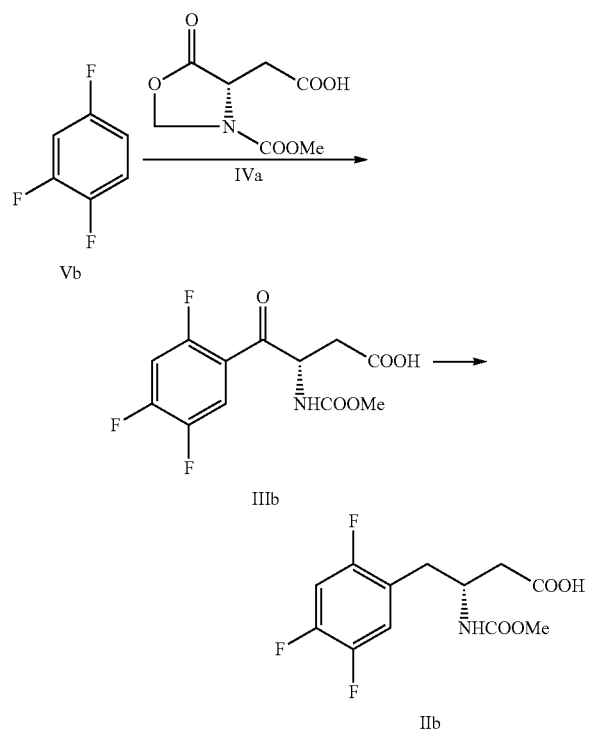

In inert atmosphere to a solution of compound IVa (21 g) in methylenechloride (50 ml) 1,2,4-trifluorobenzene Vb (26 g) was added, followed by slow addition of $AlCl_3$ (35 g) in small portions at rt under good stirring. The slurry was stirred at rt for ca. 5 hrs until the reaction was completed and no IVa was present (TLC), then carefully poured on ice (400 g) and the water phase extracted 3 times with methylenechloride (3×100 ml), the combined organic phases dried over sodium sulfate, filtered and evaporated under vacuum to give the crude compound IIIb as yellow oil: 22 g (73% yield) which was immediately used for reduction step.

To a solution of crude compound IIIb (22 g) in methanol (100 ml), after addition of conc.—HCl (1 ml) and 10% Pd—C (500 mg), the reaction mixture was hydrogenated at rt under vigorous stirring and slightly elevated hydrogen-pressure (4 bar) until the starting compound IIIb completely disappeared (5 hrs, TLC). After filtration of the catalyst, the filtrate was concentrated under vacuum to provide the title compound IIb as a yellow solid: 19.3 g (66% yield calc. from IVa) which was recrystallized from hot TBME/ethanol mixture providing pure title compound with 99.1% ee. Anal. calculated for $C_{12}H_{12}F_3NO_4$: C, 49.49; H, 4.15; F, 19.57; N, 4.81; O, 21.98. Found: C, 49.39; H, 4.25; F, 19.37; N, 4.71; O 22.18.

Example 3

(3R)-3-amino-4-(2,4,5-trifluorophenyl)-butyric acid methyl ester hydrochloride (IIc)

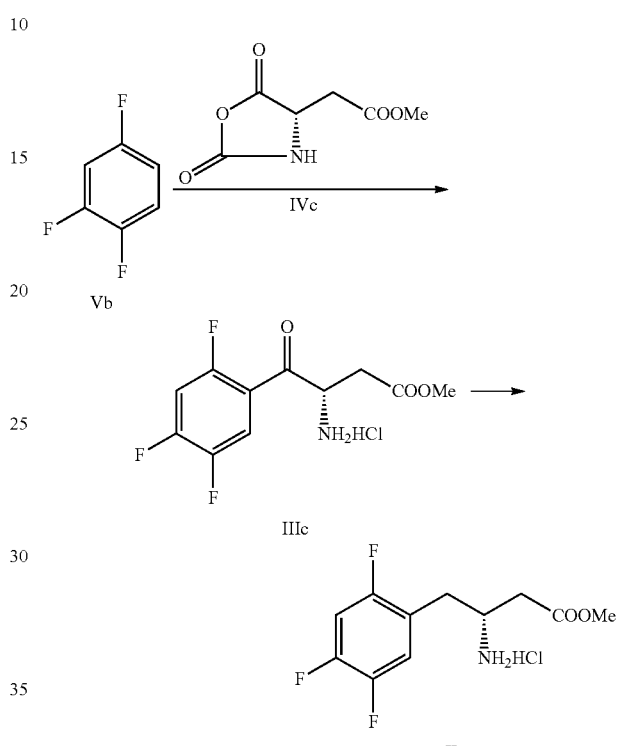

In inert atmosphere to a cooled solution of compound (IVc, 17.3 g) and 1,2,4-trifluorobenzene (75 g) in methylenechloride (100 ml) under vigorous stirring slowly in small portions $AlCl_3$ (46 g) was added that the reaction temperature did not exceed 30° C. After stirring for 5 hrs at it the slurry was poured onto ice (250 g), the aqueous phase extracted 3 times with methylenechloride (3×200 ml), the combined organic phase dried over magnesium sulfate (100 g), filtered and evaporated under reduced pressure to give hydrochloride of the compound IIIc as a yellow semi crystalline oil: 25 g (84% yield calc. to IVc) which was immediately subjected to reduction step.

Crude compound (IIIc, 25 g) was dissolved in methanol (200 ml) and after addition of 10% Pd—C (500 mg) the reaction mixture was hydrogenated at it under stirring and slightly elevated hydrogen-pressure (4 bar) until the starting compound IIIc completely disappeared (ca. 4 hrs, TLC). After filtration of the catalyst the filtrate was concentrated under reduced pressure to provide the title compound IIc as a yellow solid: 20.2 g (71% yield calc. from IVc) which was recrystallized from hot toluene/methanol mixture providing the title compound II c with 98% ee. Anal. calculated for $C_{11}H_{13}ClF_3NO_2$: C, 46.57; H, 4.62; Cl, 12.50; F, 20.09; N, 4.94; O, 11.28. Found: C, 46.32; H, 4.80; Cl, 12.52; F, 20.19; N, 5.12; O, 11.32. The analytical data of IIc have been corresponding to data reported in Tetrahedron Asymmetry 2006, 17, 205.

The invention claimed is:
1. A process for preparation of a compound of formula II, having the configuration as given in the formula,

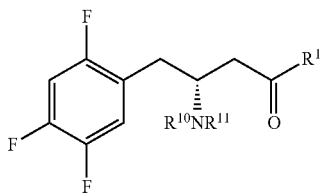

wherein $R^1$ represents hydroxy, alkoxy, aryloxy, alkylaryloxy, arylakyloxy, preferably methoxy, ethoxy, benzyloxy, or —$NR^6R^7$, wherein $R^6$ and $R^7$ are independently from each other hydrogen, lower alkyl, alkylaryl, arylalkyl, preferably —$NH_2$, —$NMe_2$, —Ndibenzyl, or in particular $R^6$ and $R^7$ can form together with N a 5- or 6-membered heterocyclic ring which may contain one or more heteroatoms selected from N or O and, which can be unsubstituted or substituted, preferably 4-alkyl-oxazolidin-2-one-3-yl, containing also a chiral center as 4(R)- or 4(S)-benzyl-oxazolidin-2-one-3-yl, or
—$NR^8OR^9$, wherein $R^8$ and $R^9$ are independently from each other hydrogen, lower alkyl, alkylaryl, arylalkyl, preferably —NMeOMe, or in particular $R^8$ and $R^9$ can form together with N and O a 5- or 6-membered heterocyclic ring which may contain one or more heteroatoms selected from N or O and, which can be unsubstituted or substituted, containing also a chiral center, and
$R^{10}$ and $R^{11}$ are independently from each other hydrogen, alkyl, aryl, alkylaryl, arylalkyl, preferably benzyl, mono-, di- or tri-methoxybenzyl, or other N-protective group, in particular one which together with N forms an amide or carbamate as —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl, —C(O)Obenzyl (Cbz) or —C(O)Otert.-butyl (BOC),
comprising following steps:
a) reaction of the compound of formula IV, having the configuration as given in the formula,

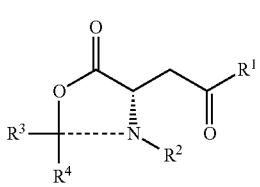

wherein $R^1$ is the same as defined for compound of formula II, and
i) when the dotted CN bond is a double bond, then $R^2$ and $R^3$ are void, and
$R^4$ is hydrogen, alkyl, aryl, alkylaryl, arylalkyl, preferably hydrogen, phenyl, benzyl, methyl, trifluoromethyl,
or
ii) when the dotted CN bond is a single bond, then
$R^2$ is hydrogen, alkyl, aryl, alkylaryl, arylalkyl, preferably benzyl, mono-, di- or tri-methoxybenzyl, or other N-protective group, in particular one which together with N forms an amide or carbamate as —C(O)alkyl, —C(O)aryl, —C(O)alkylaryl, —C(O)arylalkyl, —C(O)Oalkyl, —C(O)Oaryl, —(O)COalkylaryl, —C(O)Oarylalkyl, preferably formyl, acetyl, trifluoroacetyl, —C(O)Obenzyl (Cbz) or —C(O)Otert.-butyl (BOC, and
$R^3$ and $R^4$ are either independently from each other hydrogen, lower alkyl, aryl, alkylaryl, arylalkyl, preferably hydrogen, phenyl, trifluoromethyl, or
$R^3$ and $R^4$ are together one oxygen atom forming carbonyl function C=O,
with a compound of formula V,

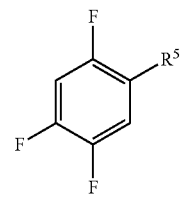

wherein $R^5$ is
i) either hydrogen, in inert aprotic organic solvent, preferably chlorinated hydrocarbons as methylenechloride or dichloroethane, or aliphatic hydrocarbons, preferably hexane or heptane, in the presence of a catalyst commonly used for Friedel-Crafts reaction, preferably bortrifluoro etherate, metal halide(s) as Al-, Zn-, lanthanide- and Bi-halides,
ii) or $R^5$ is a metal containing group especially an alkali or earth alkali metallic radical, as e.g. lithium, sodium, potassium or a group of formula Mg-halogen (Grignard reagent), —Znhalogen, -Cer(halogen)$_2$ or boronic acid as —$B(OH)_2$, but preferably —Li or —MgBr or —Mg ate complex, in inert organic solvent, preferably THF,
providing a compound of formula III, wherein $R^1$, $R^{10}$ and $R^{11}$ are the same as defined for compound of formula II;

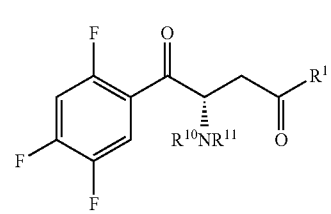

b) reduction of the carbonyl function in benzyl position in the compound of formula III, simultaneously or in separate steps;
c) protection or removal of N-protective group(s) as they are defined for $R^{10}$ and $R^{11}$ in the compound of formula II.
2. A process for preparation of a compound of formula II according to claim 1, wherein $R^1$ is hydroxy, methoxy or ethoxy, and
$R^{10}$ and $R^{11}$ are independently from each other hydrogen, benzyl, formyl, acetyl, trifluoroacetyl, —C(O)CMe$_3$, —C(O)OMe, —C(O)OEt, —C(O)OiPr, —C(O)OiBu, —C(O)Obenzyl (Cbz) or —C(O)Otert.-butyl (BOC),
comprising following steps:
a) reaction of the compound of formula IV,

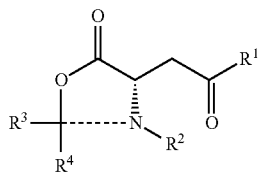

wherein the dotted CN bond is a single bond, and
$R^2$ is benzyl, formyl, acetyl, trifluoroacetyl, —C(O)CMe$_3$, —C(O)OMe, —C(O)OEt, —C(O)OiPr, —C(O)OiBu, —C(O)Obenzyl (Cbz) or —C(O)Otert.-butyl (BOC), and
$R^3$ and $R^4$ are either independently from each other hydrogen, phenyl or trifluoromethyl,
with a compound of formula V,

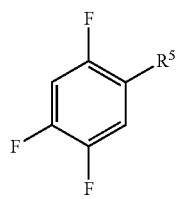

wherein $R^5$ is
i) either hydrogen, in inert aprotic organic solvent as chlorinated hydrocarbons, preferably methylenechloride or dichloroethane, or aliphatic hydrocarbons, preferably hexane or heptane, in the presence of a catalyst used for Friedel-Crafts reaction, preferably bortrifluoro etherate: metal halide(s) as Al-, Zn-, lanthanide- and Bi-halides,
ii) or $R^5$ is a metal containing group especially an alkali or earth alkali metallic radical, as e.g. lithium, sodium, potassium or a group of formula Mg-halogen (Grignard reagent), —Znhalogen, -Cer(halogen)$_2$ or boronic acid as —B(OH)$_2$, but preferably —Li or —MgBr or —Mg ate complex, in inert organic solvent, preferably THF,
providing a compound of formula III, wherein $R^1$ is hydroxy, methoxy or ethoxy, $R^{10}$ is hydrogen and $R^{11}$ is benzyl, formyl, acetyl, trifluoroacetyl, —C(O)CMe$_3$, —C(O)OMe, —C(O)OEt, —C(O)OiPr, —C(O)OiBu, —C(O)Obenzyl (Cbz) or —C(O)Otert.-butyl (BOC);

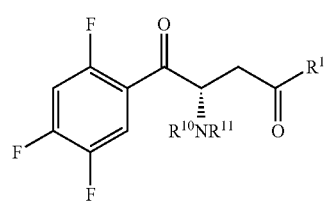

b) reduction of the carbonyl function in benzyl position in the compound of formula III, simultaneously or in separate steps;
c) removal of N-protective group as they are defined for $R^{10}$ and $R^{11}$ in the compound of formula II.

3. A process for preparation of a compound of formula II according to claim 1, wherein $R^1$ represents hydroxy, methoxy, ethoxy or benzyloxy, and
$R^{10}$ and $R^{11}$ are independently from each other hydrogen, benzyl, mono-, di- or tri-methoxybenzyl, formyl, acetyl, trifluoroacetyl, —C(O)CMe$_3$, —C(O)OMe, —C(O)OEt, —C(O)OiPr, —C(O)OiBu, —C(O)Obenzyl (Cbz) or —C(O)Otert.-butyl (BOC), comprising following steps:
a) reaction of the compound of formula IV,

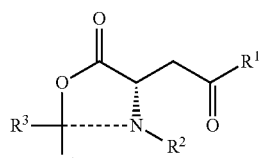

wherein the CN dotted bond is a single bond, and
$R^2$ is hydrogen, and
$R^3$ and $R^4$ are together one oxygen atom forming carbonyl function C=O,
with a compound of formula V,

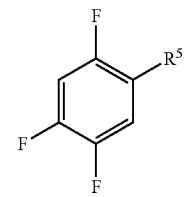

wherein $R^5$ is hydrogen, in aprotic organic solvent, preferably chlorinated hydrocarbons as methylenechloride or dichloroethane, or aliphatic hydrocarbons, preferably hexane or heptane, in the presence of a catalyst used for Friedel-Crafts reaction, preferably bortrifluoro etherate, metal halide as Al-, Zn-, lanthanide- and Bi-halides,
providing a compound of formula III, wherein $R^1$, $R^{10}$ and $R^{11}$ are the same as defined for compound of formula II;

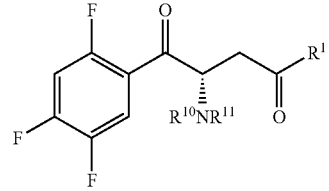

b) reduction of the carbonyl function in benzyl position in the compound of formula III, simultaneously or in separate steps;

c) protection and/or removal of N-protective group(s) as they are defined for $R^{10}$ and $R^{11}$ in the compound of formula II.

4. A process for preparation of a compound of formula II according to claim 1, wherein $R^1$ represents hydroxy, methoxy, ethoxy or benzyloxy, and $R^{10}$ and $R^{11}$ are independently from each other hydrogen, benzyl, benzoyl, formyl, acetyl, trifluoroacetyl, —C(O)CMe$_3$, —C(O)OMe, —C(O)OEt, —C(O)OiPr, —C(O)OiBu, —C(O)Obenzyl (Cbz) or —C(O)Otert.-butyl (BOC), comprising following steps:

a) reaction of the compound of formula IV,

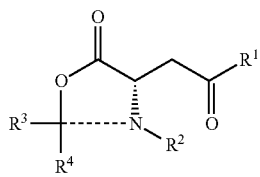

IV wherein the dotted CN bond is a double bond, and $R^2$ and $R^3$ are void, and $R^4$ is hydrogen, phenyl, benzyl, methyl, trifluoromethyl, with a compound of formula V,

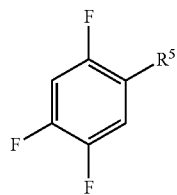

V wherein $R^5$ is hydrogen, in aprotic organic solvent, preferably chlorinated hydrocarbons as methylenechloride or dichloroethane, or aliphatic hydrocarbons, preferably hexane or heptane, in the presence of a catalyst used for Friedel-Crafts reaction, preferably bortrifluoro etherate, metal halide as Al-, Zn-, lanthanide- and Bi-halides, providing a compound of formula III, wherein $R^1$, $R^{10}$ and $R^{11}$ are the same as defined for compound of formula II;

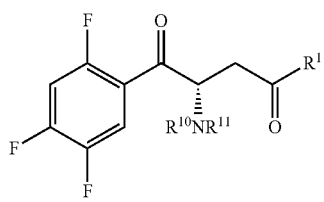

III b) reduction of the carbonyl function in benzyl position in the compound of formula III, simultaneously or in separate steps;

c) protection and/or removal of N-protective group(s) as they are defined for $R^{10}$ and $R^{11}$ in the compound of formula II.

5. A process according to anyone of claims 1, 2, 3 and 4, wherein the compound of formula III, having the configuration in the form as an enantiomerically enriched or as a racemic compound and

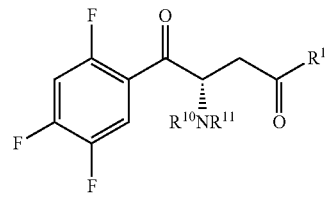

III $R^1$ is hydroxy, methoxy or ethoxy, and $R^{10}$ and $R^{11}$ are hydrogen, is subjected after the step a) to a process known as crystallization induced asymmetric transformation by adding stoichiometric amount of a chiral acid H—X, preferably (1R or 1S)-10-camphorsulfonic acid or (D or L)-tartaric acid or (D or L)-dibenzoyl tartaric acid, (1R or 1S)-3-bromocamphor-8-sulfonic acid, (+ or −)-1,1'-binaphtyl-2,2'-diyl-hydrogenphosphate or (D or L)-mandelic acid, in the presence of a catalytic amount of an aldehyde, preferably aromatic aldehyde as benzaldehyde, in a suitable solvent, preferably in alcohol, dialkylether, aromatic hydrocarbon, acetone, acetic acid, acetonitrile or nitromethane, where the HX salt of the (S)-configurated compound of formula III has only limited solubility, collecting the enantiomerically pure HX-salt of (S)-configurated compound of formula III from the precipitate, converting this salt into (S)-compound of formula III by treatment with suitable organic or inorganic base, and using it in the following steps b) and c).

6. A process for preparation of a compound of formula III, having the configuration as given in the formula,

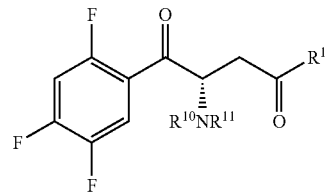

III wherein $R^1$ is hydroxy, methoxy or ethoxy and $R^{10}$ and $R^{11}$ are hydrogen, comprising reaction of a compound of formula III, in the form as either enantiomerically enriched or as a racemic compound, with stoichiometric amount of a chiral acid H—X, preferably (1R or 1S)-10-camphorsulfonic acid or (D or L)-tartaric acid or (D or L)-dibenzoyl tartaric acid, 1R or 1S)-3-bromocamphor-8-sulfonic acid, (+ or −)-1,1'-binaphtyl-2,2'-diyl-hydrogenphosphate or (D or L)-mandelic acid, in the presence of a catalytic amount of an aldehyde, preferably aromatic aldehyde as benzaldehyde, in a suitable solvent, preferably in alcohol, dialkylether, aromatic hydrocarbon, acetone, acetic acid, acetonitrile or nitromethane, where HX salt of the (S)-configurated compound of formula III has only limited solubility, collecting the enantiomerically pure HX-salt of (S)-configurated compound of formula III from the precipitate and converting this salt into (S)-compound of formula III by treatment with suitable organic or inorganic base.

\* \* \* \* \*